United States Patent [19]

Selvarajan et al.

[11] 4,100,167

[45] Jul. 11, 1978

[54] PRODUCTION OF 1-AMINOALKANE-1, 1-DIPHOSPHONIC ACIDS USING PHOSPHOROUS ACID AND NITRILES IN A NON-AQUEOUS SYSTEM

[75] Inventors: Radhakrishnan Selvarajan, Oak Park; Edward G. Ballweber, Glenwood, both of Ill.

[73] Assignee: Nalco Chemical Company, Oak Brook, Ill.

[21] Appl. No.: 794,887

[22] Filed: May 9, 1977

[51] Int. Cl.$^2$ .................... C07D 213/73; C07F 9/38
[52] U.S. Cl. ..................... 260/296 R; 260/295 AM; 260/295.5 A; 260/502.5
[58] Field of Search ............. 260/296 R, 502.5, 297 P, 260/502.4 R, 502.4 P, 294.9

[56] References Cited

U.S. PATENT DOCUMENTS

| | | | |
|---|---|---|---|
| 3,870,750 | 3/1975 | Wollmann et al. | 260/502.5 |
| 3,919,296 | 11/1975 | Schindler | 260/502.5 |

OTHER PUBLICATIONS

Eastman Organic Chemical Bulletin, vol. 48, (1) pp. 1–3 (1976).

*Primary Examiner*—Alan L. Rotman
*Attorney, Agent, or Firm*—John G. Premo; Robert A. Miller; Barry W. Sufrin

[57] ABSTRACT

1-aminoalkane--1, 1-diphosphonic acids of the formula,

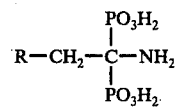

may be produced in good yield by reacting a nitrile of the formula,

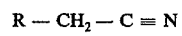

$$R - CH_2 - C \equiv N$$

with at least 2 moles of phosphorous acid in the presence of a high boiling hydrocarbon oil at a temperature ranging between 140°–170° C without a catalyst. In the above formula, R is hydrogen, alkyl, aryl, arylalkyl, substituted aryl, substituted alkyl, and substituted arylalkyl. These compounds show anti-corrosive activity.

3 Claims, No Drawings

PRODUCTION OF 1-AMINOALKANE-1, 1-DIPHOSPHONIC ACIDS USING PHOSPHOROUS ACID AND NITRILES IN A NON-AQUEOUS SYSTEM

This invention relates to a method of producing compounds having the formula,

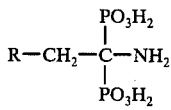

These compounds are 1-aminoalkane-1,1-diphosphonic acids. In the above formula, R may be hydrogen, alkyl, aryl, arylalkyl, substituted aryl, substituted alkyl, and substituted arylalkyl. In a preferred embodiment of the invention, R contains not more than 20 carbon atoms.

The compound wherein R is hydrogen is described in the literature and this compound, 1-aminoethane 1,1-diphosphonic acid, when combined with zinc salts, is known to be a corrosion inhibitor for aqueous systems. See U.S. Pat. No. 3,668,138.

The pertinent patent prior art is as follows:

U.S. Pat. No. 3,919,296 Schindler relates to a process for the production of 1,1-diphosphonic acids employing hydrogen halide as a catalyst. The patentee also uses a mole ratio $H_3PO_3$ as compared with nitriles in a maximum value of 1.5:1. Furthermore, the reaction temperatures are lower than the present invention using ranges of 0°–30° C and −20° to +5° C if HCl is used. The maximum temperature of reaction when the cooling means are not used or are removed is 90° C as in Example 5, which is substantially below the range of the present invention.

German Pat. No. 1,002,355, in the production of phosphonic acids, utilizes a temperature range substantially lower than the present applicants or in the range 60°–70° C. Again, the patentee uses phosphorous trihalide as a phosphorylating agent coupled with $H_3PO_3$.

U.S. Pat. No. 3,565,949 Cummins is directed to a cleaning composition but Examples 1 and 2 give process parameters. These parameters show that phosphorous trihalides, especially phosphorous tribromide, are used as phosphorylating agents at temperatures of 40°–50° C, which is later changed to 90°–100° C. Both temperature ranges are substantially below that of the present invention.

British Pat. No. 995,462 deals with metal complexes of amino phosphonic acids. The acids are prepared by reacting phosphorous trihalides with organic nitriles and the temperatures are 0°–100° C, utilizing about 2 moles phosphorous trihalides per mole of nitrile. This patent shows reaction temperatures substantially below that of the present invention.

The references deal with synthesis of compounds of the present invention by different routes, showing different phosphorylating agents, different temperature ranges of reaction, and addition of catalyst where no catalyst is used in the present invention.

The process of the present invention resides in reacting a nitrile of the formula, $R-CH_2-C \equiv N$ (Formula II below) with at least 2 moles of phosphorous acid at a temperature ranging between 140°–170° C in the presence of a high boiling hydrocarbon liquid for a period of time sufficient to convert at least a portion of the nitrile into the corresponding diphosphonic acid. In the process no catalyst is used and phosphorous acid is used as the sole phosphorylating agent. In a specific embodiment of the invention, the reaction is conducted in the presence of oil-soluble emulsifiers which allows the finished products to be produced as an emulsion.

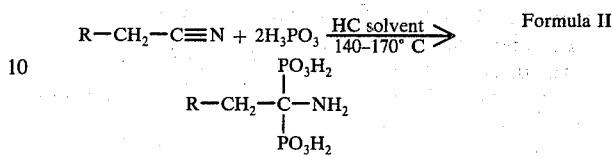

THE NITRILE REACTANT

As previously indicated, the nitrile reactant as set forth in Formula II may be selected from a wide range of nitriles that are commercially available or which may be readily synthesized. A preferred starting material is acetonitrile. The process of the invention produces finished diphosphonic acids in good yields when the starting nitrile is an aliphatic nitrile of not more than 20 carbon atoms. Thus, propionitrile and acrylonitrile are admirably suited for use as a starting material in the process of this invention.

In addition to using aliphatic nitriles of the type described, the invention is capable of converting a variety of nitriles into their corresponding amino diphosphonic acid derivatives of the types shown in Formula I. Thus, it is possible to use as starting nitriles propionitrile, benzonitrile, phenylacetonitrile, cyanoacetic acid, acrylonitrile, and dinitriles separated by 4–6 carbon atoms or more.

A variety of fatty nitriles and mixed fatty nitriles such as cocoa, tallow, and oleoyl nitriles may be readily converted by the process of the invention. Aromatic substituted nitriles, such as benzonitrile and the like, may be used as starting materials. Polar substituted aliphatic nitriles or arylalkyl substituted nitriles where the aromatic nuclei contains a polar substituent may also be used. Thus, aliphatic nitriles containing sulphonic acid groups, oxy groups either in the form of ether linkage or as a keto grouping may be employed. Arylalkyl nitriles wherein the aromatic ring contains substituents such as sulphonic acid groups, halo groups, and the like may be employed.

Nitriles of heteroaromatics may also function. It has been found that with benzonitrile, wherein the nitrile group is linked directly to an aromatic carbon atom, very little reaction occurs between the nitrile grouping and the phosphorous acid. However, on the contrary, cyanopyridines with the substituent at positions 2, 3, or 4 do afford the phosphonic acids in very good yields.

THE STARTING PHOSPHOROUS ACID

It is desirable that the phosphorous acid contain no more than 10% by weight of water and, preferably, it should contain 5% by weight or less of water. Anhydrous phosphorous acid is preferred in conducting the reaction more fully described hereinafter.

The amount of phosphorous acid used should be at least 2 moles per mole of nitrile or nitrile group present in the starting nitrile compound.

REACTION TEMPERATURES AND TIME

To insure good yields, it is necessary that the reaction be conducted at a temperature of at least 140° to about 185° C with a preferred temperature range being 140°–170° C. It should be noted that the temperature should not be allowed to exceed 190° C due to the exothermic nature of the reaction.

When the temperature is maintained within the ranges thus specified, the reaction time may be varied between as little as ½ hour up to as long as 24 hours, with typical reaction times being within the range of 1–12 hours. The reaction time may not be specified with any degree of certainty since it is dependent upon the temperature involved, the starting nitrile, and the other variables used in conducting the reaction.

THE HYDROCARBON LIQUID

The use of a hydrocarbon liquid as a suspending medium for the nitrile and the phosphorous acid represents one of the most novel features of the invention. A high boiling liquid hydrocarbon is preferred and is defined as a hydrocarbon liquid boiling at at least 175° C at standard temperature and pressure. This liquid operates as a heat transfer media, thus allowing good temperature control to be maintained. It keeps the product and reactants from settling to the bottom of the reactor where the reactants tend not to react due to poor physical contact. A very useful hydrocarbon solvent is a paraffinic hydrocarbon oil ISOPAR M (Exxon, b.p. 210° C). Any high boiling hydrocarbon liquid with a boiling point of at least 175° C may be used, such as heavy mineral oils, lubricating oils, and the like.

The amount of hydrocarbon oil used in relation to the reactants cannot be set forth with any degree of specificity. It should be an amount sufficient to allow the reactants to be suspended therein in the form of a slurry or an emulsion. In some instances, as little as 20–30% by weight of the oil based on the reactants is adequate.

Since the reaction is conducted at elevated temperatures and certain of the starting materials, such as the lower nitriles, tend to vaporize, it is important that the reaction be conducted in a pressure vessel. In most instances, autogenous pressures are sufficient although in certain instances the use of elevated pressures tends to speed up the reaction. Also, reaction vessels should be equipped with adequate cooling means, such as coils, since the reaction tends to be exothermic and, therefore, requires cooling to control the reaction temperature within the ranges previously set forth herein.

THE EMULSIFIERS

In certain instances it is beneficial to incorporate with the reactants and the hydrocarbon oil from about 1–5% oil-soluble dispersing agent or emulsification agent. These materials may be either cationic or nonionic or mixtures thereof. When such materials are used, they must be carefully selected since, due to the elevated temperatures employed in the reaction and the high degree of reactivity of phosphorous acid, such emulsifiers must be able to withstand these two parameters of the reaction; otherwise, they are not suitable for use in the practice of the invention. The purpose of these agents is to produce the finished organic aminophosphonic acids in a form whereby they may be readily handled in large scale commercial equipment.

For instance, when acetonitrile is reacted with 2 moles of phosphorous acid with ISOPAR-M as the organic solvent, the finished product is a hard, dense solid mass that is only difficultly dispersed in water. When a proper surfactant is used during the course of the reaction, the finished product is dispersed in the oil and is much more easily removed from a commercial reactor.

A particularly useful blend of surfactants comprises the utilization of a fatty substituted oxazoline quaternary and an ethoxylated nonyl phenol. This combination or blend of surfactants is a tallow substituted oxazoline quaternary and an ethylene oxide adduct of nonyl phenol combined in a 1:1 ratio and in a preferred case this combination was added to the reaction medium at a 2.5–5.0% level based on solids. A preferred specific combination is a blend of ALKATERGE T, a substituted oxazoline wax (Commercial Solvents Corp.), with TRITON X-45, which is an octylphenoxy polyethoxy ethanol (100) (Rohm and Haas).

It is noted that the pressure of the reactions increases along with the temperature of the reaction mixture, reaches a maximum, and drops rapidly, following the exotherm. In the particular reaction noted in Formula III the pressure drop is interpreted as the consumption of acetonitrile and formation of the iminophosphonic acid.

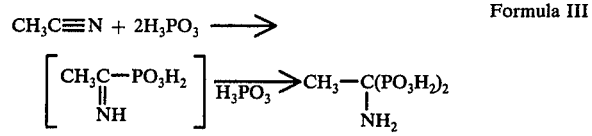

Formula III

EXAMPLES

Generalized Procedure

The subject nitriles were reacted with anhydrous phosphorous acid in the molar ratio 1:2 at 150°±10° C, uniformly stirred under nitrogen atmosphere and at ambient pressure. ISOPAR-M (Exxon) was used as a suspending medium at a level such that the solids constituted 50±5% concentration. A combination of emulsifiers, vis. nonyl alkylphenol and fatty alkyl oxazoline quaternary compound, in equal weight ratio and constituting 5% based on the solids, were used as wetting agents to bring about dispersal of solids. In order to form a precipitate, the reaction products were subsequently mixed with excess ethanol or methylethyl ketone and the precipitated solid was crushed, filtered, washed with acetone and dried under vaccum at 60° C overnight.

EXAMPLE 1

Acetonitrile and Phosphorous Acid

A mixture of acetonitrile (8.2 g, 0.2 mole), phosphorous acid (32.8 g, 0.4 mole), ISOPAR-M (20 g), and the above wetting agents (0.5 g each) was reacted for 3 hours at 150° C. The mixture was cooled to 80° C and water (50 g) was added. The colorless emulsion broke to give colorless granular 1-amino-1,1-diphosphono ethane, 29 g (71% yield), m.p. 270°–271° C (decomposition).

EXAMPLE 2

A 1 liter autoclave was charged with a mixture of phosphorous acid (328 g, 4.0 moles), ISOPAR-M (200 g), and the wetting agents (10 g each). The mixture was pressurized with nitrogen and heated to 150° C. Acetonitrile (82 g, 2.0 moles) was pumped in slowly over 1 hour period so as to avoid a violent reaction. The mixture was kept heated for 2 hours thereafter and the temperature was closely controlled. Then water (250 g) was pumped in and the reaction mixture cooled. The product 1-amino-1,1-diphosphono ethane was collected and washed with water, followed by acetone. Colorless and granular product, 61% yield, was obtained.

EXAMPLE 3

A 1 liter autoclave was charged with a mixture of acetonitrile (61.5 g, 1.5 moles), ISOPAR-M (300 g), and the wetting agents (7.5 g each). The mixture was pressurized with nitrogen and heated to 150° C. Melted phosphorous acid (246 g, 3.0 moles) was pumped into the reactor through 15 minutes. The reaction was continued for 3 hours, maintaining the temperature at 150° C. Water (300 g) was pumped in and the product was collected after cooling. Colorless crystals of 1-amino-1,1-diphosphono ethane was obtained as fine grains, 76% yield.

EXAMPLE 4

A mixture of propionitrile (5.5 g, 0.1 mole), phosphorous acid (16.4 g, 0.2 mole), ISOPAR-M (22 g), and wetting agents (0.5 g each) was heated under nitrogen at ambient pressure for 2 hours at 150° C. The product was worked up with ethanol. Colorless crystals of 1-amino-1,1-diphosphono propane (52% yield), m.p. 282° C was obtained.

EXAMPLE 5

Phenylacetonitrile (5.6 g, 0.05 mole) was mixed with phosphorous acid (8.2 g, 1.0 mole), ISOPAR-M (20 g), and wetting agents (0.25 g each). The mixture was heated at ambient pressure for 4 hours at 150° C. The product was worked up with ethanol to get colorless crystals of 1-amino-1,1-diphosphono-2-phenyl ethane (40%), m.p. 238° C (decomposition).

EXAMPLE 6

Acrylonitrile (5.3 g, 0.1 mole) mixed with phosphorous acid (16.4 g, 0.2 mole), ISOPAR-M (20 g), and wetting agents (0.5 g each) was kept heated for 5 hours at 150° C. Following an exotherm, the refluxing of acrylonitrile ceased. The product was worked up with ethanol to obtain a pale yellow, water-soluble product in 100% yield. It was found to be a mixture of oligomeric phosphonic acids and 1-amino-1-1-3 triphosphonopropane.

EXAMPLE 7

3-Butenonitrile (6.7 g, 0.1 mole) mixed with phosphorous acid (16.4 g, 0.2 mole), ISOPAR-M (23 g), and emulsifiers (0.5 g each) was kept heated at 160° C for 5 hours. The product was worked up with methylethyl ketone. A pale yellow and hygroscopic solid in 100% yield was obtained. By gpc it was formed to be oligomers, chiefly dimer and trimer, of the bisphosphonic acid.

EXAMPLE 8

A mixture of 2-cyanopyridine picolinonitrile, 10.4 g, 0.1 mole), phosphorous acid (16.4 g, 0.2 mole), ISOPAR-M (26 g) and the wetting agents (0.6 g each) was kept heated at 150° C for 2 hours. The mixture was worked up with ethanol to get brown crystals of amino-(2 pyridyl)methane diphosphonic acid, 78%, contaminated with traces of tripicolinic acid amide (ir, nmn).

EXAMPLE 9

3-Cyanopyridine (nicotinonitrile, 10.4 g, 0.1 mole) mixed with phosphorous acid (16.4 g, 0.2 mole), ISOPAR-M (26 g) and the wetting agents (0.6 g each) was kept heated at 150° C for 2 hours. Upon work up with ethanol, pale yellow water-soluble crystals of amino-(3-pyridyl)methane diphosphonic acid, 82%, contaminated with nicotinamide (ir) was obtained.

EXAMPLE 10

A mixture of cyanoacetic acid (4.3 g, 0.5 mole), phosphorous acid (8.2 g, 0.1 mole), ISOPAR-M (20 g), and the wetting agents (0.25 g each) was heated at 165° C for 2 hours. The product was worked up with acetone to get yellow crystals of 1-amino-1,1-diphosphono-2-carboxy ethane, m.p. 255° C (decomposition), 55%, associated with traces of impurities.

We claim:

1. A process for producing 1-amino-alkane-1,1-diphosphonic acids of the formula,

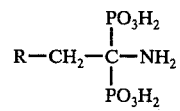

which comprises reacting a nitrile of the formula, [R—CH₂—C=N]R—CH₂—C≡N, with at least 2 moles of phosphorous acid in the presence of a high boiling hydrocarbon liquid suspending agent at a temperature ranging between 140°–170° C. for a period of time to sufficiently convert the nitrile and the phosphorous acid into the aminoalkane-1,1-diphosphonic acid and then recovering said aminoalkane-1,1-diphosphonic acid and wherein in the above formula R is selected from the group consisting of hydrogen, alkyl with 1–18 carbon atoms, phenyl, phenylalkyl where alkyl has 1–18 carbon atoms, substituted phenyl wherein the phenyl moiety contains a sulfonic acid group or halo group, and pyridyl.

2. The process of claim 1 wherein R is a cyanopyridine substituted at positions 2, 3, or 4.

3. The process of claim 1 where R contains not more than 18 carbon atoms.